(12) United States Patent
Rescorl et al.

(10) Patent No.: US 9,877,878 B2
(45) Date of Patent: *Jan. 30, 2018

(54) REUSABLE SHIELD AND LINER FOR USE DURING MENSTRUATION

(71) Applicant: Days for Girls International, Lynden, WA (US)

(72) Inventors: Linda L. Rescorl, Ocala, FL (US); Celeste Mergens, Lynden, WA (US); Janice Mae Bode, Lynden, WA (US); Cindy Murdock, Los Alamos, NM (US); LaPriel Stein, Rexburg, ID (US)

(73) Assignee: Days for Girls International, Lynden, WA (US)

( * ) Notice: Subject to any disclaimer, the term of this patent is extended or adjusted under 35 U.S.C. 154(b) by 824 days.

This patent is subject to a terminal disclaimer.

(21) Appl. No.: 14/445,301

(22) Filed: Jul. 29, 2014

(65) Prior Publication Data

US 2016/0030255 A1  Feb. 4, 2016

(51) Int. Cl.
| | | |
|---|---|---|
| *A61F 13/70* | (2006.01) | |
| *A61F 13/76* | (2006.01) | |
| *A61F 13/74* | (2006.01) | |
| *A61F 13/49* | (2006.01) | |
| *A61F 13/472* | (2006.01) | |
| *A61F 13/15* | (2006.01) | |
| *A61F 13/56* | (2006.01) | |

(52) U.S. Cl.
CPC .. *A61F 13/49003* (2013.01); *A61F 13/15268* (2013.01); *A61F 13/472* (2013.01); *A61F 13/5605* (2013.01); *A61F 2013/15276* (2013.01); *A61F 2013/16* (2013.01)

(58) Field of Classification Search
CPC ...... A61F 13/15268; A61F 2013/15276; A61F 13/505
USPC .................................................. 604/385.15
See application file for complete search history.

(56) References Cited

U.S. PATENT DOCUMENTS

| | | | | | |
|---|---|---|---|---|---|
| 1,695,153 | A | * | 12/1928 | Nelson .................... | A61F 13/64 604/397 |
| 1,992,075 | A | * | 2/1935 | Kennard ............... | A61F 13/505 604/397 |
| 2,494,307 | A | * | 1/1950 | Niolon ............. | A61F 13/49003 604/385.15 |
| 2,571,357 | A | * | 10/1951 | Gemora .................. | A61F 13/64 604/397 |
| 2,684,677 | A | * | 7/1954 | Pinney ............. | A61F 13/49003 604/385.15 |
| 2,840,078 | A | * | 6/1958 | Smith ..................... | A61F 13/64 604/397 |
| 3,117,577 | A | * | 1/1964 | Mosier .................... | A61F 13/64 604/399 |
| 3,225,765 | A | * | 12/1965 | Mosier .................... | A61F 13/64 604/397 |
| 4,044,769 | A | * | 8/1977 | Papajohn ................ | A61F 13/72 604/385.19 |
| 4,664,663 | A | * | 5/1987 | Brier ....................... | A61F 13/47 604/387 |
| 5,181,915 | A | * | 1/1993 | Smith ............... | A61F 13/49004 604/358 |

(Continued)

*Primary Examiner* — Susan Su

(74) *Attorney, Agent, or Firm* — DLA Piper LLP (US)

(57) ABSTRACT

A reusable shield and liner for use by a woman during menstruation is disclosed. The liner is octagonal in shape and comprises two or more layers. The shield contains one water-resistant layer.

20 Claims, 7 Drawing Sheets

(56) References Cited

U.S. PATENT DOCUMENTS

| | | | | | |
|---|---|---|---|---|---|
| 5,360,422 | A * | 11/1994 | Brownlee | A61F 13/49004 | 604/385.14 |
| 5,752,946 | A * | 5/1998 | Boberg | A61F 13/47 | 604/373 |
| 5,814,037 | A * | 9/1998 | Coates | A61F 13/49004 | 604/385.15 |
| 6,443,933 | B1 * | 9/2002 | Suzuki | A61F 13/4942 | 604/358 |
| 6,764,477 | B1 * | 7/2004 | Chen | A61F 13/4702 | 604/385.14 |
| 7,166,095 | B1 * | 1/2007 | Coates | A61F 13/505 | 604/385.14 |
| 8,894,626 | B2 * | 11/2014 | Beck | A61F 13/505 | 604/385.01 |
| 8,968,264 | B2 * | 3/2015 | Coates | A61F 13/49 | 604/385.14 |
| 9,011,403 | B2 * | 4/2015 | De Bruin | A61F 13/4906 | 604/385.14 |
| 2001/0034510 | A1 * | 10/2001 | Shinkai | A61F 13/15211 | 604/385.01 |
| 2003/0216705 | A1 * | 11/2003 | Coates | A61F 13/505 | 604/386 |
| 2004/0158225 | A1 * | 8/2004 | Coates | A61F 13/495 | 604/397 |
| 2004/0236298 | A1 * | 11/2004 | Coates | A61F 13/476 | 604/385.04 |
| 2006/0224136 | A1 * | 10/2006 | Martinez | A61F 13/472 | 604/385.15 |
| 2008/0021433 | A1 * | 1/2008 | Allison-Rogers | A61F 13/5616 | 604/397 |
| 2008/0108964 | A1 * | 5/2008 | Edwall | A61F 13/49011 | 604/385.3 |
| 2009/0299313 | A1 * | 12/2009 | Knightingale | A61F 13/15268 | 604/367 |
| 2010/0168709 | A1 * | 7/2010 | Hodgkin | A61F 13/49004 | 604/385.14 |
| 2010/0318057 | A1 * | 12/2010 | Yakem | A61F 13/505 | 604/396 |
| 2011/0015600 | A1 * | 1/2011 | Pham | A61F 13/505 | 604/367 |
| 2011/0178492 | A1 * | 7/2011 | Coates | A61F 13/505 | 604/385.101 |
| 2012/0029459 | A1 * | 2/2012 | Hallouin | A61F 13/49413 | 604/385.15 |
| 2012/0109092 | A1 * | 5/2012 | Austin | A61F 13/505 | 604/385.03 |
| 2013/0023846 | A1 * | 1/2013 | Beck | A61F 13/505 | 604/385.14 |
| 2013/0172844 | A1 * | 7/2013 | Coates | A61F 13/505 | 604/385.14 |
| 2014/0114273 | A1 * | 4/2014 | Sierra | A61F 13/665 | 604/397 |

* cited by examiner

REUSABLE SHIELD AND LINER FOR USE DURING MENSTRUATION

TECHNICAL FIELD

A reusable shield and liner for use by a woman during menstruation is disclosed.

BACKGROUND OF THE INVENTION

In many developing countries, women do not have access to affordable menstruation supplies. Women often are chastised and isolated during the menstruation process, and in some countries, it is customary for women to miss school or work during the menstruation process.

What is needed is an affordable, reusable device to assist women during the menstruation process.

SUMMARY OF THE INVENTION

A reusable shield and liner for use by a woman during menstruation is disclosed.

DETAILED DESCRIPTION OF THE PREFERRED EMBODIMENTS

Figure 1:
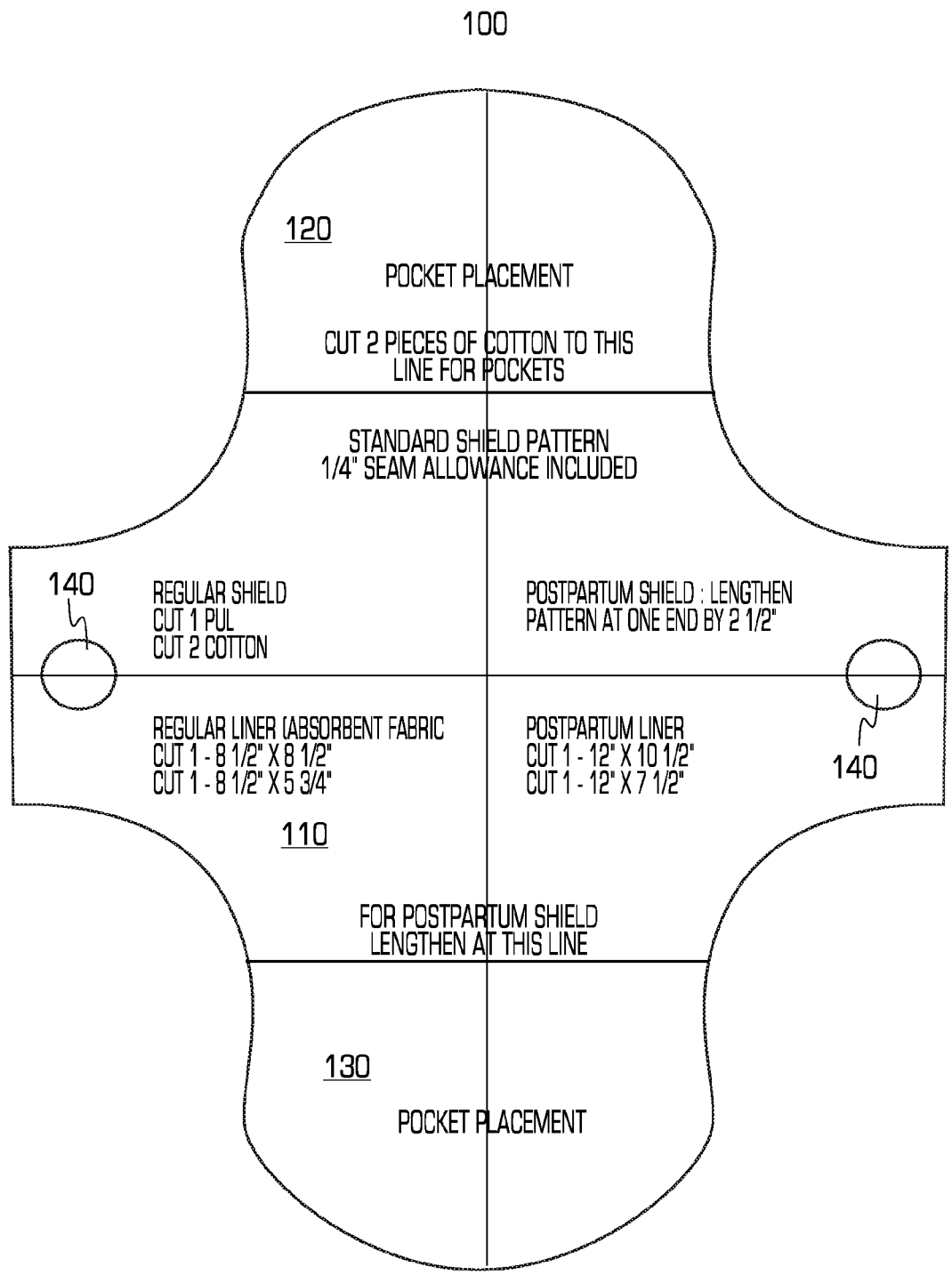
FIG. 1 depicts a prior art reusable shield developed by the applicant.

With reference to FIG. 1, prior art reusable shield 100 developed by the applicant is depicted. Shield 100 comprises a first piece 110 in the general shape shown in FIG. 1, a second piece 120 attached to the first piece 110 as shown, and a third piece 130 attached to the first piece as shown. First piece 110, second piece 120, and third piece 130 comprise pieces of cloth, preferably cotton. Second piece 120 and third piece 130 are sewn, adhered, or attached using other means to first piece 110 to form pockets. Shield 100 also comprises attachment mechanism 140, which can comprise a snap, button, Velcro, or other known attachment mechanism.

Figure 2:
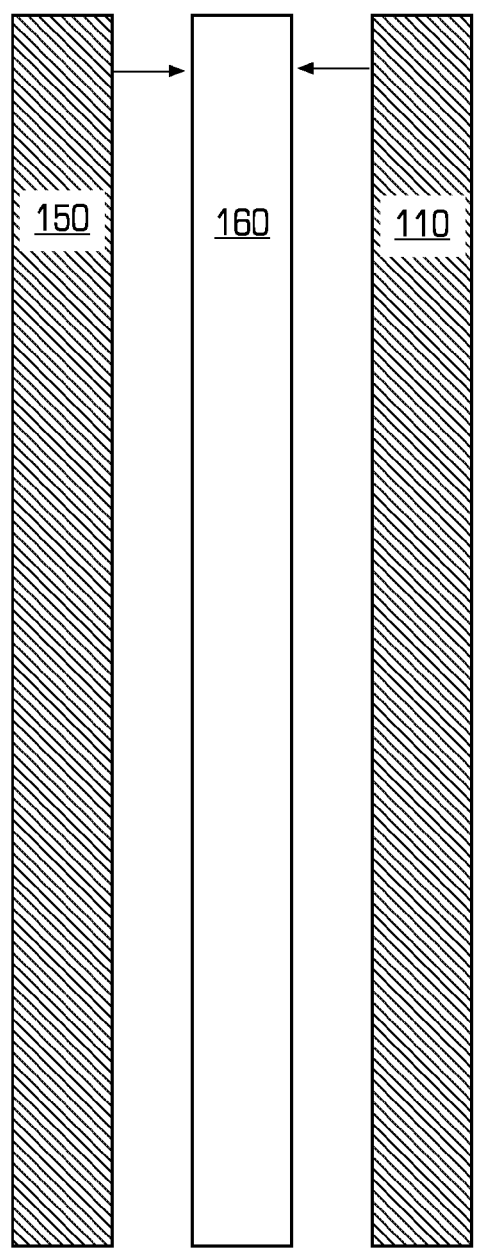
FIG. 2 depicts a side view of the prior art reusable shield of FIG. 1.

With reference to FIG. 2, first piece 110 also is attached to fourth piece 160, which is made of water-resistant material such as polyurethane laminate or other water-resistant material. Fourth piece 160 is of the same shape as first piece 110, and the side of first piece 110 opposite the side attached to second piece 120 and third piece 130 is sewn, adhered, or attached using other means to fourth piece 160. On the opposite site of fourth piece 160 is fifth piece 150, which can be identical to first piece 110. Fourth piece 160 and fifth piece 150 are sewn or adhered together or attached using other means. First piece 110, fourth piece 160, and fifth piece 150 can be sewn or adhered together or attached using other means in a contiguous manner.

Figure 3:
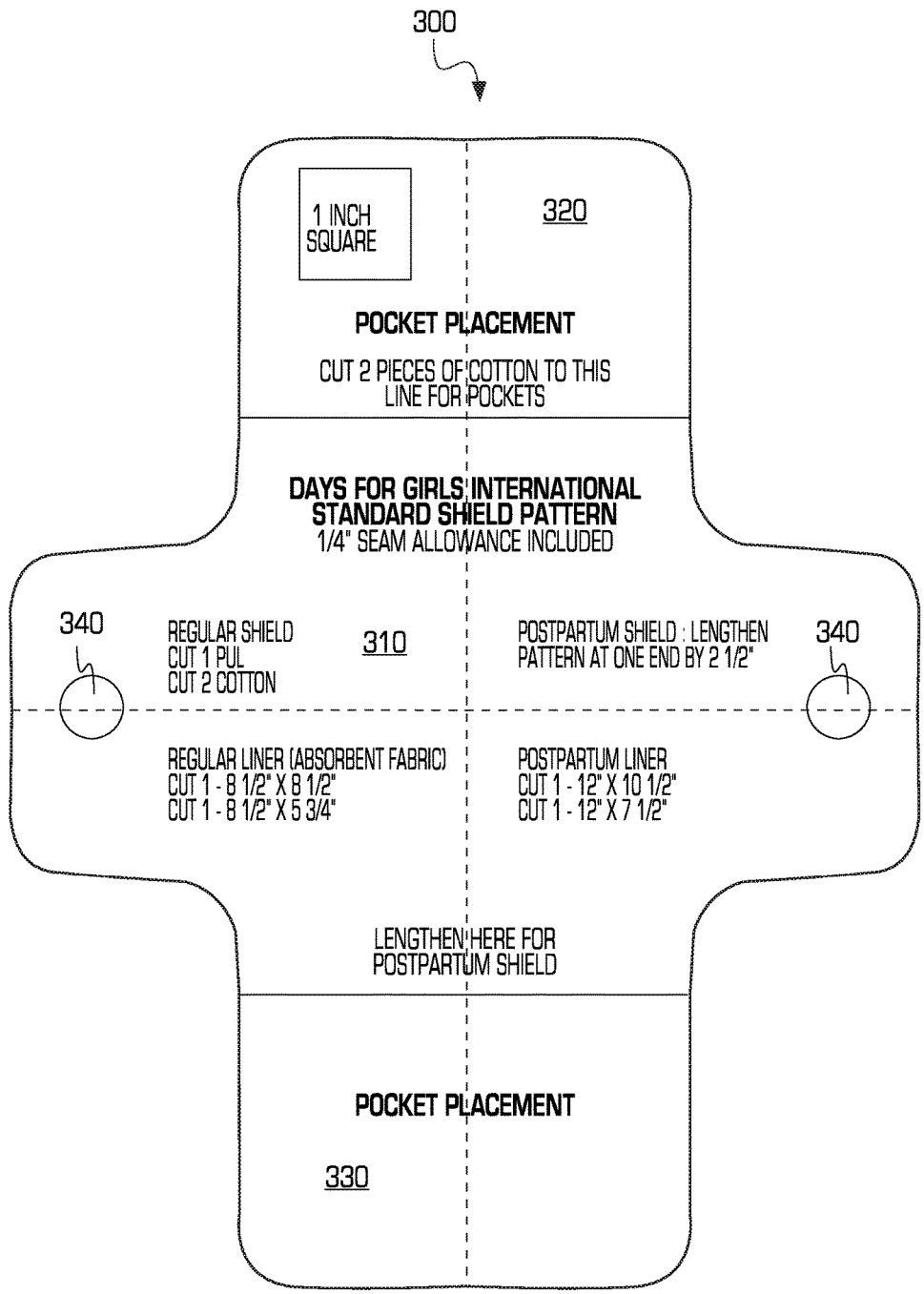
FIG. 3 depicts an embodiment of a reusable shield developed by the applicant.

With reference to FIG. 3, an embodiment of an improved reusable shield 300 is depicted. Shield 300 comprises a first piece 310 in the general shape shown in FIG. 3, a second piece 320 attached to the first piece 310 as shown, and a third piece 330 attached to the first piece as shown. First piece 310, second piece 320, and third piece 330 comprise pieces of cloth, preferably cotton. Second piece 320 and third piece 330 are sewn, adhered, or attached using other means to first piece 310 to form pockets. Shield 300 also comprises attachment mechanism 340, which can comprise a snap, button, Velcro, or other known attachment mechanism.

Figure 4:
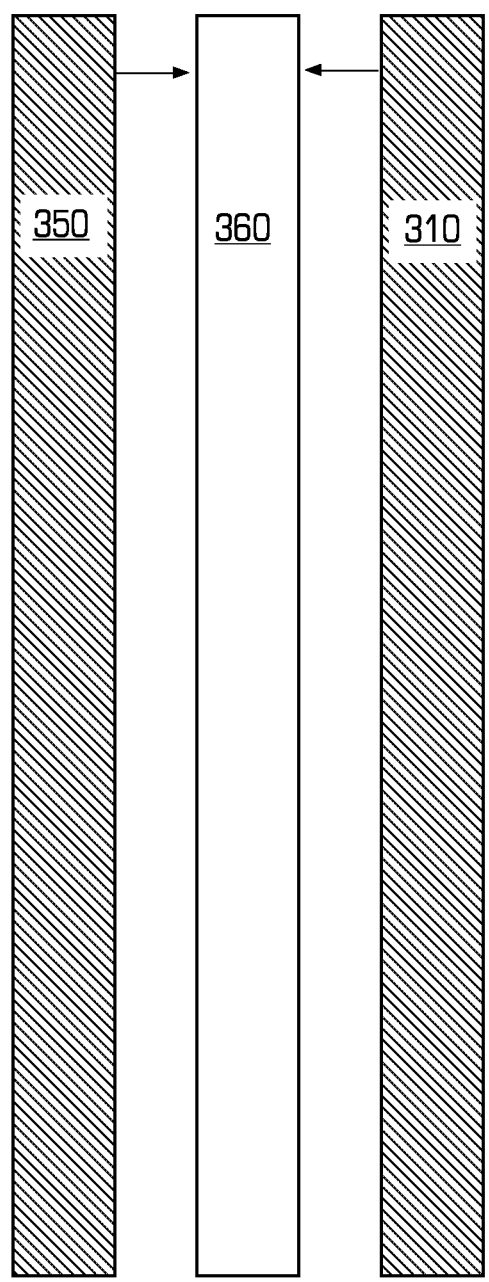
FIG. 4 depicts a side view of the reusable shield of FIG. 3.

With reference to FIG. 4, first piece 310 also is attached to fourth piece 360, which is made of water-resistant material such as polyurethane laminate or another water-resistant material. Fourth piece 360 is of the same shape as first piece 310, and the side of first piece 310 opposite the side attached to second piece 320 and third piece 330 is sewn, adhered, or attached using other means to fourth piece 360. On the opposite site of fourth piece 360 is fifth piece 350, which can be identical to first piece 310. Fourth piece 360 and fifth piece 350 are sewn or adhered together or attached using other means. First piece 310, fourth piece 360, and fifth piece 350 can be sewn or adhered together or attached using other means in a contiguous manner.

Figure 5:
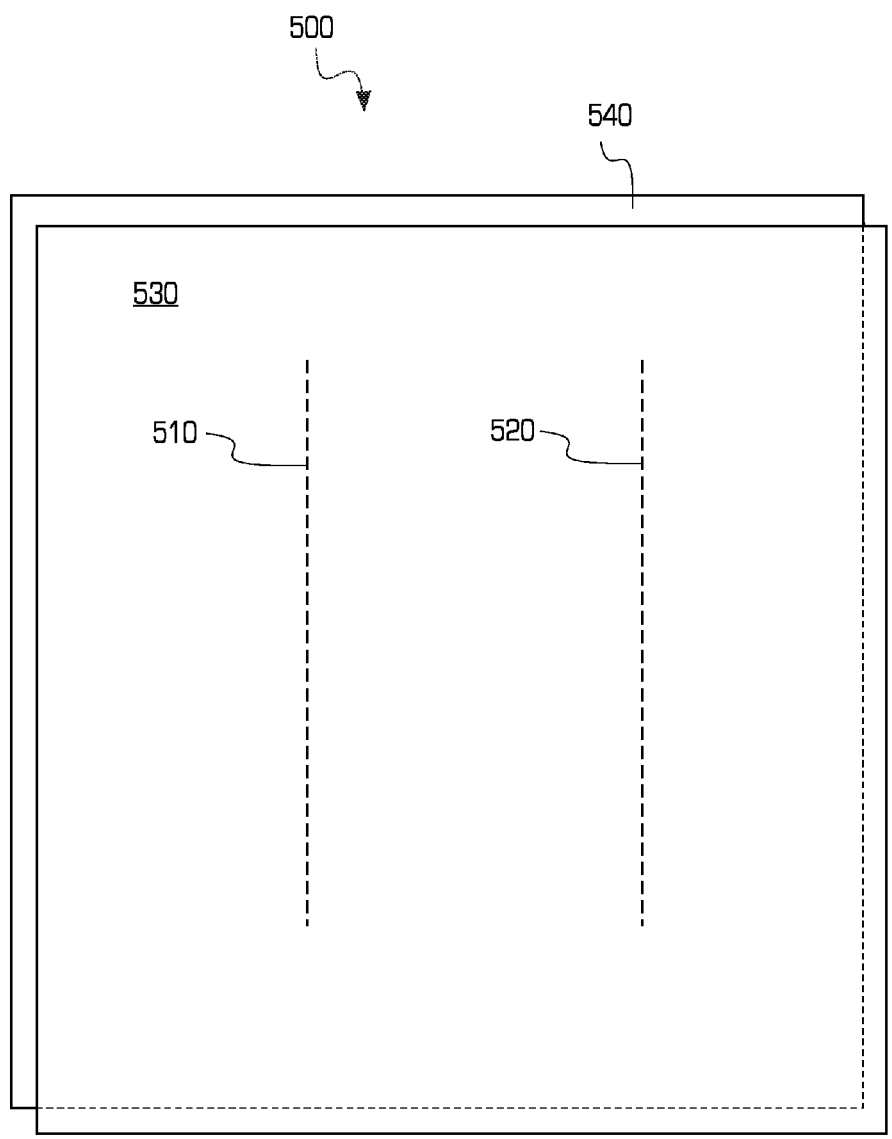
FIG. 5 depicts a prior art reusable liner developed by the applicant.

With reference to FIG. 5, prior art reusable liner 500 is depicted. Liner 500 has a generally square shape and can be folded along fold lines 510 and 520. Liner 500 comprises first layer 530, and optionally includes second layer 540 as well. First layer 530 and second layer 540 are made from cloth, preferably cotton or flannel. First layer 530 and second layer 540 are sewn or adhered together or attached using other means.

Figure 6:
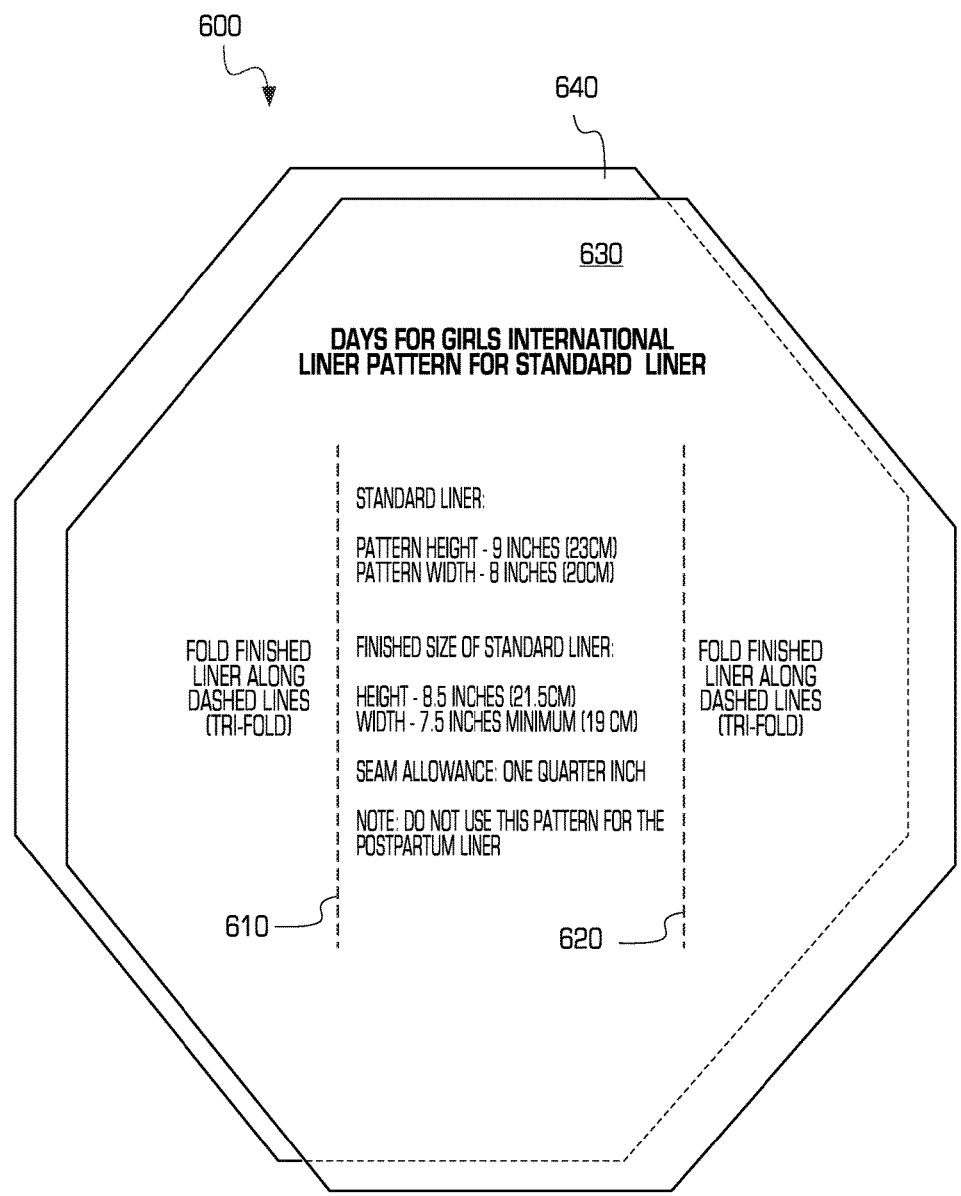
FIG. 6 depicts an embodiment of a reusable liner developed by the applicant.

With reference to FIG. 6, an embodiment of an improved liner 600 is depicted. Liner 600 has a generally octagonal shape and can be folded along fold lines 610 and 620. Liner 600 is an improvement over liner 500 because it is less bulky in certain areas and is more comfortable for a woman to wear. Liner 600 comprises first layer 630 and optionally includes second layer 640. First layer 630 and second layer 640 are made from cloth, preferably cotton or flannel. First layer 630 and second layer 640 are sewn or adhered together or attached using other means.

Figure 7:
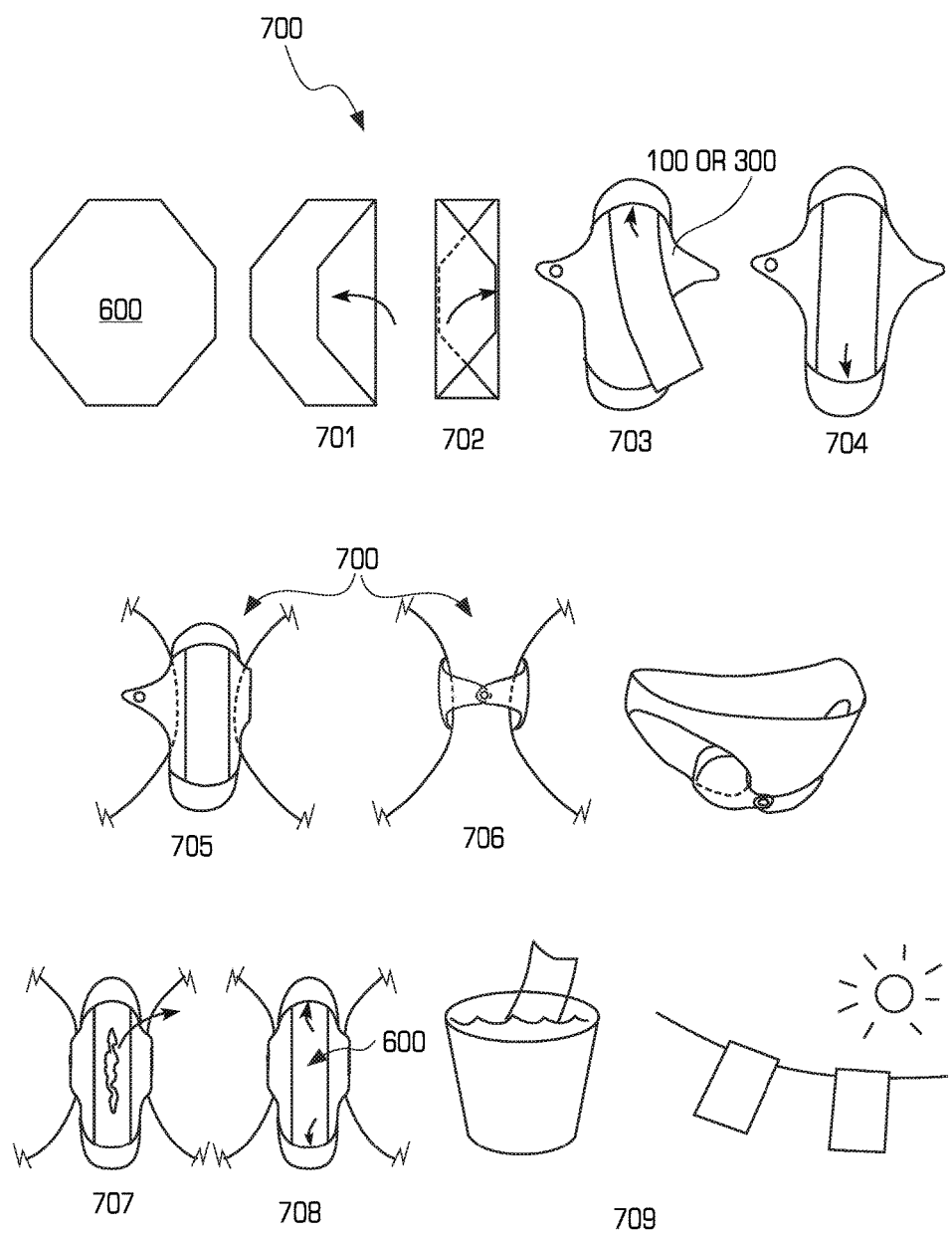
FIG. 7 depicts a method for assembling and using a shield and liner.

With reference to FIG. 7, a method 700 of using liner 600 in conjunction with shield 100 or shield 300 is shown. Liner 600 is folded along fold line 620 (step 701) and then is folded along fold line 610 (step 702) to create a generally rectangular shape. Liner 600 is then inserted into shield 100 (or shield 300) by inserting one end of liner 600 into the pocket formed by first piece 110 and second piece 120 (or first piece 310 and second piece 320) (step 703) and inserting the other end of liner 600 into the pocket formed by first piece 110 and third piece 130 (or first piece 310 and third piece 330) (step 704). Liner 600 and shield 100 or shield 300 are then attached to underwear 700 as shown in FIG. 7 using attachment mechanism 140 (or attachment mechanism 340) (steps 705 and 706). The combination of underwear 700, liner 600, and shield 100 or shield 300 can then be worn by a woman. After use, liner 600 can be removed (step 707) a new liner 600 inserted as described previously (step 708) and then old liner 600 can be washed (step 709). Thereafter, old liner 600 can be reused.

References to the present invention herein are not intended to limit the scope of any claim or claim term, but instead merely make reference to one or more features that may be covered by one or more of the claims. Structures, processes and numerical examples described above are exemplary only, and should not be deemed to limit the claims. It should be noted that, as used herein, the terms "over" and "on" both inclusively include "directly on" (no intermediate materials, elements or space disposed there between) and "indirectly on" (intermediate materials, elements or space disposed there between).

What is claimed is:

1. A reusable liner and shield, comprising:
    a liner comprising one or more layers of cloth of octagonal shape, the one or more layers of cloth comprising a first portion, a second portion, and a third portion, wherein the second portion is folded along a first fold line over the first portion and the third portion is folded along a second fold line over the first portion and wherein part of the third portion lays over part of the second portion;
    wherein the liner is rectangular in shape and having a front end, a rear end, and a central portion between the front and rear ends, wherein the front and rear ends have less bulk than the central portion;
    a shield comprising:
        a first piece;
        a second piece attached to a first side of the first piece to form a first pocket,
            wherein the first pocket contains a first opening for receiving the liner; and a third piece attached to the first side of the first piece to form a second pocket, wherein the second pocket contains a second opening for receiving the liner; and
        a fourth piece attached to a second side of the first piece;
    wherein the front end of the liner is removably placed in the first pocket through the first opening and the rear end of the liner is removably placed in the second pocket through the second opening; and
    wherein during use, the central portion of the liner has an upper surface configured to contact a user and a lower surface configured to contact the first piece of the shield.

2. The liner and shield of claim 1, wherein the fourth piece is made of polyurethane laminate.

3. The liner and shield of claim 1, wherein the cloth comprises cotton.

4. The liner and shield of claim 3, wherein the first piece, second piece, and third piece each comprise cotton.

5. The liner and shield of claim 1, wherein the shield comprises a fifth piece attached to the fourth piece.

6. The liner and shield of claim 5, wherein the fifth piece comprises cotton.

7. The liner and shield of claim 1, wherein the shield further comprises an attachment mechanism.

8. The liner and shield of claim 7, wherein the attachment mechanism comprises a snap.

9. The liner and shield of claim 7, wherein the attachment mechanism comprises a button.

10. The liner and shield of claim 7, wherein the attachment mechanism comprises hook and loop fasteners.

11. A method of using a reusable liner and shield, comprising:
    forming a rectangular liner from an octagonal cloth by folding the octagonal cloth along a first fold line, wherein a first portion of the cloth is on one side of the first fold line and a second portion of the cloth is on another side of the first fold line such that the second portion lays over the first portion after the folding is complete;
    folding the octagonal cloth along a second fold line, wherein the first portion of the cloth is on one side of the second fold line and a third portion of the cloth is on another side of the second fold line such that the third portion lays over the first portion and part of the third portion lays over part of the second portion after the folding is complete;
    wherein the rectangular liner has a front end, a rear end, and a central portion between the front and rear ends, wherein the front and rear ends have less bulk than the central portion;
    inserting the front end of the liner into a first pocket in a shield;
    inserting the rear end of the liner into a second pocket in a shield such that the central portion of the liner has an upper surface configured to contact a user and a lower surface configured to contact the shield;
    attaching the shield to an undergarment using an attachment mechanism; and
    removing the liner from the shield.

12. The method of claim 11, wherein the cloth comprises a first layer and a second layer.

13. The method of claim 11, wherein the shield comprises a piece of polyurethane laminate.

14. The method of claim 13, wherein the shield comprises a first piece of cotton attached to a first side of the piece of polyurethane laminate.

15. The method of claim 14, wherein the shield comprises a second piece of cotton attached to a second side of the piece of polyurethane laminate.

16. The method of claim 11, wherein the attachment mechanism comprises a snap.

17. The method of claim 11, wherein the attachment mechanism comprises a button.

18. The method of claim 11, wherein the attachment mechanism comprises hook and loop fasteners.

19. The method of claim 11, further comprising: washing the liner.

20. The method of claim 18, further comprising: reusing the liner in the shield.

* * * * *